(12) United States Patent
Cao et al.

(10) Patent No.: US 11,464,424 B2
(45) Date of Patent: Oct. 11, 2022

(54) CLOUD PLATFORM

(71) Applicant: BMC Medical Co.,Ltd., Beijing (CN)

(72) Inventors: Zhixin Cao, Beijing (CN); Zhi Zhuang, Beijing (CN); Qingkai Meng, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 226 days.

(21) Appl. No.: 15/744,798

(22) PCT Filed: Nov. 15, 2016

(86) PCT No.: PCT/CN2016/105925
§ 371 (c)(1),
(2) Date: Jan. 14, 2018

(87) PCT Pub. No.: WO2017/084559
PCT Pub. Date: May 26, 2017

(65) Prior Publication Data
US 2018/0206763 A1    Jul. 26, 2018

(30) Foreign Application Priority Data

Nov. 17, 2015    (CN) ......................... 201510792558.2

(51) Int. Cl.
*A61B 5/08*    (2006.01)
*A61B 5/00*    (2006.01)
(Continued)

(52) U.S. Cl.
CPC .............. *A61B 5/08* (2013.01); *A61B 5/0022* (2013.01); *A61B 5/7264* (2013.01); *G16H 20/40* (2018.01);
(Continued)

(58) Field of Classification Search
CPC .. A61B 5/08–095; A61B 5/0002; A61B 5/746
See application file for complete search history.

(56) References Cited

U.S. PATENT DOCUMENTS 6,283,923 B1 *   9/2001   Finkelstein ............ A61B 5/411
                                                          600/532
2005/0251056 A1 *   11/2005   Gribkov ............... A61B 5/0452
                                                          600/509
(Continued)

FOREIGN PATENT DOCUMENTS

CN        101133954 A     3/2008
CN        101933838 A     1/2011
(Continued)

OTHER PUBLICATIONS

Reddy et al. "Review of ventilatory techniques to optimize mechanical ventilation in acute exacerbation of chronic obstructive pulmonary disease." Int J Chron Obstruct Pulmon Dis. Dec. 2007; 2(4): 441-452. (Year: 2007).*

*Primary Examiner* — Meredith Weare
(74) *Attorney, Agent, or Firm* — Bayramoglu Law Offices LLC

(57) ABSTRACT

A cloud platform comprises a receiving unit and a processing unit. The receiving unit is configured to receive at least one user respiration data set sent by at least one respirator device in at least one uploading cycle. The processing unit is configured to acquire a first user respiration data set sent by a user of one respirator device among at least one respirator device in one uploading cycle, statistically analyze the first user respiration data set on the basis of a stable state value set of the user, and send an alarm signal when the statistical analysis result is determined to be that the first user respiration data set meets a data exception standard. The disclosure provides an on-line user respiration data analysis solution in combination with disease diagnosis of an off-line respiration system, so that the worsening of a patient's conditions can be possibly found in time.

4 Claims, 4 Drawing Sheets

(51) Int. Cl.
*G16H 20/40* (2018.01)
*G16H 40/67* (2018.01)
*G16H 50/20* (2018.01)
*A61M 16/00* (2006.01)

(52) U.S. Cl.
CPC ............ *G16H 40/67* (2018.01); *G16H 50/20* (2018.01); *A61B 5/746* (2013.01); *A61M 16/00* (2013.01); *A61M 2205/18* (2013.01); *A61M 2205/3553* (2013.01); *A61M 2205/3584* (2013.01); *A61M 2205/84* (2013.01)

(56) References Cited

U.S. PATENT DOCUMENTS

| | | | | |
|---|---|---|---|---|
| 2007/0179347 | A1* | 8/2007 | Tarassenko | A61B 5/0002 600/300 |
| 2008/0091089 | A1* | 4/2008 | Guillory | A61B 5/0478 600/301 |
| 2012/0016251 | A1 | 1/2012 | Zhang et al. | |
| 2012/0179061 | A1* | 7/2012 | Ramanan | A61M 16/024 600/538 |
| 2014/0088373 | A1 | 3/2014 | Phillips et al. | |
| 2015/0178463 | A1* | 6/2015 | Criner | G06F 19/3456 705/2 |
| 2016/0089089 | A1* | 3/2016 | Kakkar | G06F 19/325 600/484 |
| 2016/0302671 | A1* | 10/2016 | Shariff | A61B 5/0022 |
| 2017/0238867 | A1* | 8/2017 | Javed | A61B 5/087 |
| 2018/0184945 | A1* | 7/2018 | Borel | A61B 5/746 |

FOREIGN PATENT DOCUMENTS

| | | |
|---|---|---|
| CN | 202505352 U | 10/2012 |
| CN | 102793538 A | 11/2012 |
| CN | 103040524 A | 4/2013 |
| CN | 104207753 A | 12/2014 |
| CN | 104759043 A | 7/2015 |
| CN | 104840204 A | 8/2015 |
| CN | 105031786 A | 11/2015 |
| CN | 105232049 A | 1/2016 |
| EP | 2008581 A2 | 12/2008 |
| EP | 2465434 A1 | 6/2012 |

* cited by examiner

CLOUD PLATFORM

CROSS-REFERENCE TO RELATED APPLICATIONS

This application is the national stage of International Application No. PCT/CN2016/105925 filed Nov. 15, 2016, which claims the benefit of priority from Chinese Patent Application No. CN201510792558.2, filed Nov. 17, 2015, the entirety of which are incorporated herein by reference.

TECHNICAL FIELD

The present disclosure relates to the technical field of on-line data analysis, and more specifically, to a cloud platform.

BACKGROUND

Along with the development of the Internet technologies, cloud products and cloud-based services are booming in all industries. On-line medical treatment has become one of the new development trends in the medical industry. On the one hand, in combination with data analysis technologies, it is possible to comprehensively analyze and evaluate massive user respiration data uploaded by various medical machine terminals such as a respirator at the cloud server or cloud client of a cloud platform, to provide remote monitoring on rehabilitation and management of chronic diseases of patients at home, and to reduce treatment cost for patients.

The respirator is a medical device which can replace, control and change the normal physiological respiration of people and increase pulmonary ventilation volume, can improve, prevent and cure ventilation failure, and is used to treat diseases such as COPD (Chronic Obstructive Pulmonary Diseases), bronchiectasia, phthisis, occupational pulmonary diseases, neuromuscular diseases, obesity and thoracocyllosis and concurrent ventilation failure. Among the diseases, COPD is a common disease resulting in ventilation failure because of a high morbidity and no effective medical treatment, causing serious disease burden.

Chronic obstructive pulmonary disease (COPD) is a pulmonary disease that features incompletely reversible airflow obstruction and the conditions of the majority of patients progressively worsen. In the later stage, besides the lungs, the COPD can also affect many important body organs such as the heart, brain and kidneys. In recent years, the morbidity and case fatality rate of the COPD have risen continuously. According to the predictions of the World Bank, the ranking of the worldwide disease economic burden caused by COPD will rise from being the 12th in 1990 to the 5th in 2020, and the ranking of the global cause of death will rise from the 6th in 1990 to the 3rd in 2020.

Due to disturbance of gas diffusion due to changes in the anatomical structure of a respiratory unit, oxygen deficits and $CO_2$ retention, the COPD weakens the hypoxic response, and together cause respiratory muscle fatigue, it is difficult to treat the COPD with regular medicines and achieve a satisfactory effect. BiPAP (Bi-Level Positive Airway Pressure) ventilation is a non-invasive ventilation technology where ventilation is completed with an oral-nasal mask or a nasal mask. BiPAP can effectively improve ventilation, improve the diffusion and oxygenation functions, aid correcting the circulation dysfunction in patients, and therefore can quickly treat hyoxemia and hypercapnia, improve clinical symptoms and reduce the use of trachea cannula. BiPAP avoids a series of complications caused by trachea cannula for invasive mechanical ventilation, such as respirator associated pneumonia, helps disease observation and respiratory tract management, and improves control over infection of patients with AECOPD (Acute Exacerbation of Chronic Obstructive Pulmonary Diseases). With BiPAP, the patients have less pain, can bear the treatment, avoid or reduce the use of sedatives, and can also shorten the length of stay of the patients in hospital, thus improving the life quality of patients and reduce the hospitalization expenses and the case fatal rate of patients. At present, BiPAP respirator has become a well-known effective means for assisting treatment, and has been widely applied to intensive care units, public wards and households.

A patient with COPD suffers from acute Exacerbation for about 0.5-3.5 times each year. Due to respiratory tract infection, airway obstruction and respiratory muscle fatigue, a patient with AECOPD easily tends to suffer type-II respiratory failure, resulting in a rise in case fatal deaths and treatment difficulties. AECOPD seriously affects the living quality and disease progress of patients and increases the social economic burden, can speed up the pulmonary function decline in patients and involves the increase in the case fatal rate of the inpatients. AECOPD is a process of acute onset, and patients with COPD have acute exacerbation of respiratory symptoms. COPD management normally focuses on the prevention and treatment of AECOPD.

However, AECOPD symptoms and pulmonary functions of patients vary a lot, concerning with the basic pulmonary functions, exacerbation factors and individual sensitivities. Usually, the basic standard of AECOPD is that patients cannot be cured with OTC medicines and need emergency treatment or outpatient treatment under the conditions of coughing, expectoration, gasping exacerbation and obvious decline in mobility that affect basic life (taking food and falling asleep). The patients with AECOPD basically need doctors to adjust the treatment solutions, so that the severity degree of the diseases of the patients must be accurately evaluated. Effective evaluation methods for patients with AECOPD have not been found yet it prior art, usually causing difficulties in treatment after the patients suffer AECOPD.

SUMMARY

One of the technical problems to be solved by the embodiments of the disclosure is how to find out possible exacerbation of the respiratory diseases of patients in early stage through early monitoring, for example possible AECOPD state of the patients with COPD.

According to the embodiments of the disclosure, all kinds of respiration data uploaded by a respirator that is used by a patient in the records of a cloud server can be statistically analyzed and then alarms or prompts on situations where the patient may have AECOPD can be given according to the analysis result. After the patient receives the alarms or prompts (or a doctor receives the alarms or prompts and informs the patient), the patient can go to the hospital and the doctor can make a diagnosis and verify if the AECOPD appears. However, it should be noted that, the inventor also conceives that the embodiments of the disclosure can also apply to diagnosis of severe symptoms of other respiratory diseases in the early stage.

According to an aspect of the present disclosure, there is provided a cloud platform, comprising a receiving unit and a processing unit. The receiving unit is configured to receive at least one user respiration data set sent by at least one respirator device in at least one uploading cycle. The processing unit is configured to acquire a first user respiration data set sent by a user of one respirator device among at least one respirator device in one uploading cycle, statistically analyze the first user respiration data set on the basis of a stable state value set of the user, and send an alarm signal when a statistical analysis result is determined to be that the first user respiration data set meets a data abnormal standard.

According to another aspect of the present disclosure, there is provided a method for alarming abnormal user respiration data, comprising: receiving at least one user respiration data set sent by at least one respirator device in at least one uploading cycle; acquiring a first user respiration data set sent by a user of one respirator device among at least one respirator device in one uploading cycle, statistically analyzing the first user respiration data set on the basis of a stable state value set of the user, and sending an alarm signal when a statistical analysis result is determined to be that the first user respiration data set meets a data abnormal standard.

According to another aspect of the present disclosure, there is provided a device for alarming abnormal user respiration data, comprising: a receiving device for receiving at least one user respiration data set sent by at least one respirator device in at least one uploading cycle; an acquisition device for acquiring a first user respiration data set sent by a user of one respirator device among at least one respirator device in one uploading cycle, an alarm device for statistically analyzing the first user respiration data set on the basis of a stable state value set of the user, and sending an alarm signal when a statistical analysis result is determined to be that the first user respiration data set meets a data abnormal standard.

According to another aspect of the present disclosure, there is provided a program, comprising readable codes, wherein when the readable codes are operated in a device, the device executes the method for alarming abnormal user respiration data according to the embodiments of the present disclosure.

According to another aspect of the present disclosure, there is provided a readable medium, storing the program according to the embodiments of the present disclosure.

The various embodiments of the disclosure provide a set of on-line user respiration data analysis solutions in combination with off-line respiratory disease monitoring, so the disease exacerbation of patients can be found in time in the early stage.

In embodiments given on the basis of COPD, the respiration data set of the current cycle of a user and/or historical respiration data sets can be analyzed, and alarms on the possibility of the onset of the AECOPD of the user can be given according to the analysis results, so patients can go to the hospital in time or doctors can diagnose the conditions before the onset of the AECOPD.

From the detailed description in conjunction with the attached drawings below, the advantages and characteristics of the disclosure, together with operation principles and modes, become apparent. Among all attached drawings described in the whole context, similar elements have similar numbers.

DETAILED DESCRIPTION OF THE EMBODIMENTS

The contents of the present disclosure are completely described below with reference to the attached drawings which display embodiments according to the disclosure. However, the embodiments can be executed in various ways and cannot be interpreted as limits to the disclosure. On the contrary, the embodiments make the contents of the disclosure clear and complete, and comprehensively express the scope of the contents of the disclosure to those skilled in the art.

The following are detailed description of the disclosure in conjunction with attached drawings.

Figure 1:
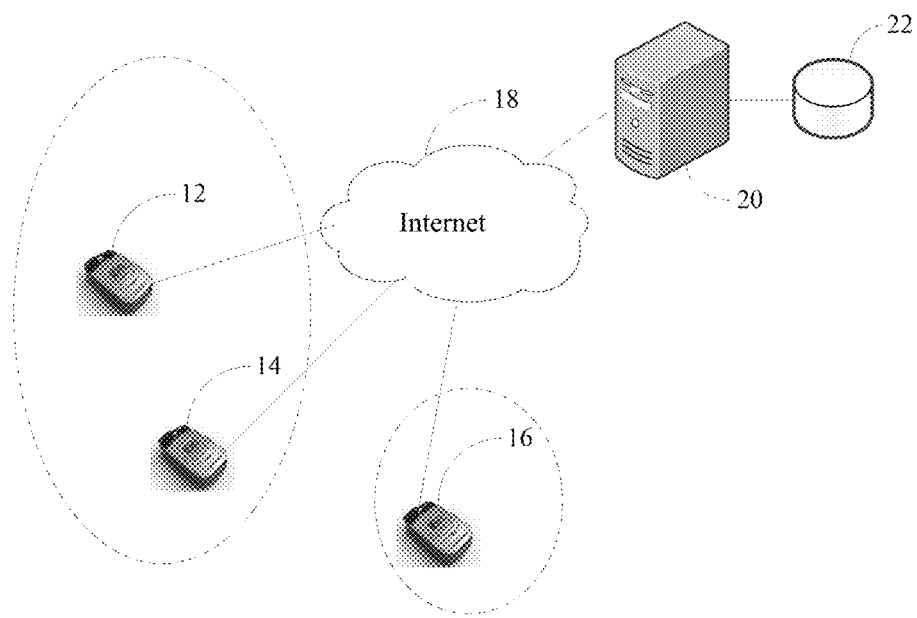
FIG. 1 is a schematic view of a system where embodiments according to the disclosure can be achieved.

First, referring to FIG. 1, which illustrates a schematic view of a system 100 in which all embodiments of the disclosure can be executed. As shown in FIG. 1, the system 100 may include respirators 12, 14 and 16, a cloud server 20 and a database 22 which is connected with the cloud server 20, wherein the respirators 12, 14 and 16 are respectively connected with the Internet 18 through data links, and then connected to the cloud server 20 through communication links. In FIG. 1, the respirators 12 and 14 may be placed at the homes of different patients and the respirator 16 may be placed in a hospital.

The data links in FIG. 1 may be wired or wireless connection means of any types, including but not limited to, power wires, cables, power wires, TV broadcast, remote wireless connection, short-distance wireless connection, etc. The connecting network between the respirators 12, 14 and 16 and the cloud server 20 is shown as the Internet in FIG. 1, but the embodiments of the disclosure may also apply to other networks that include, but are not limited to, mobile phone network, wireless local area networks (WLAN), self-organized network, Ethernet LAN, Token loop LAN, wide area network, and any combinations of those networks with the Internet.

Communication technologies or communication standards for communication among all devices may include, but not be limited to, CDMA (Code Division Multiple Access), GSM (Global System for Mobile communication), UMTS (Universal Mobile Telecommunications System), TDMA (Time Division Multiple Access), FDMA (Frequency Division Multiple Access), TCP/IP (Transmission Control Protocol/Internet Protocol), SMS (Short Message Service), MMS (Multimedia Message Service), email, IMS (Instant Messaging Service), Bluetooth, IEEE 802.11, etc. The communication devices involved for realizing the present invention in various embodiments may use various media to perform communication, where the media may include, but be not limited to, wireless, infrared, laser, cable connections, etc.

The respirators 12, 14 and 16 may be respirators of any types, including household non-invasive respirators such as single-level respirators and dual-level respirators, and may also be therapy invasive respirators in hospitals, which upload user respiration data sets generated when users use the respirators to the cloud server. The user respiration data uploaded by the respirators are data related to the respiration state of users, and the user respiration data sets are sets of values of respiration state indices of various types (real time or special moment). The respirators 12, 14 and 16 may also include various relevant monitoring devices that can record user respiration data respectively, for example devices for monitoring blood oxygen data, thoracico-abdominal data, electroencephalogram data, heart beat data, etc.

The respirator 12 or 14 that a user can use at home uploads the user respiration data set generated when the user uses the respirator to the cloud server 20. Alternatively or additionally, the user respiration data set generated when the user uses the respirator 16 in the hospital is also uploaded to the cloud server 20.

The cloud server 20 may analyze a certain uploaded user respiration data set to verify if the current respiration state of the user is abnormal. The user respiration data may be stored in a database 22 which is connected to the cloud server 20, and may also be stored in a memory of the cloud server 20.

Figure 2:
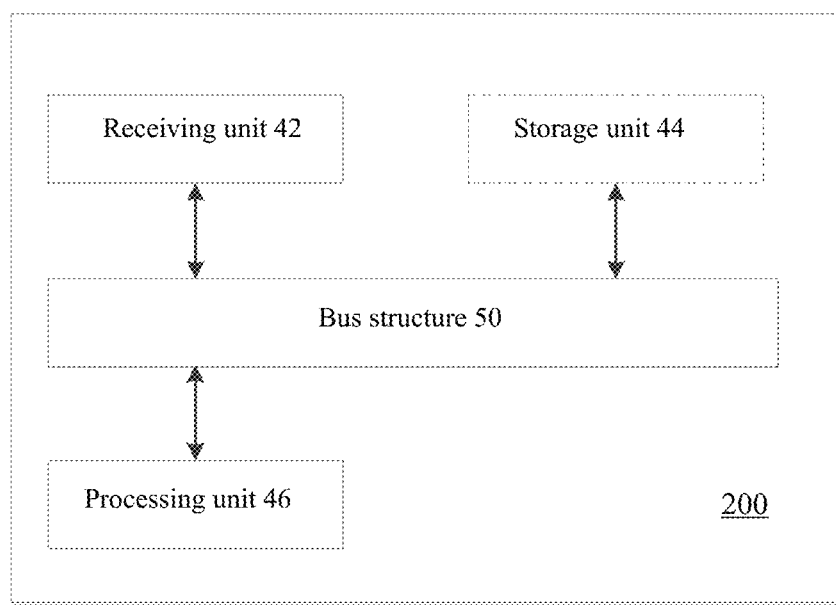
FIG. 2 is a block diagram of a cloud server in one embodiment according to the disclosure.

FIG. 2 is a block diagram of a cloud server 200 in one embodiment according to the disclosure. The cloud server 200 may include a receiving unit 42, a storage unit 44 and a processing unit 46 that are connected with one another through a system bus 50. As a computer system, the cloud server 200 may also include other units not shown in the drawings, for example a RAM, a ROM, various hardware controllers (for example, hard disc controller, keypad controller, serial port controller, parallel port controller, display controller), a hard disc, a keypad, a serial port device, a parallel port device, display, etc.

The receiving unit 42 may include a transmitter and/or a receiver which may be a RF interface, a Bluetooth interface and/or IrDa interface for providing communication services. The processing unit 46 may be any commercially available CPU, digital signal processor (DSP) or any other digital programmable logic device. The storage unit 44 may be a RAM, ROM, EEPROM, flash memory, hard disc or any combinations thereof. It should be understood that, the block diagram in FIG. 2 is shown for the purpose of illustration instead of limiting the disclosure. In some circumstances, some devices may be added or reduced. It should be understood that, the receiving unit 42, the storage unit 44 and the processing unit 46 in FIG. 2 are all positioned at the cloud server 200, but the functions to be realized by the cloud server on the cloud platform may also be distributed to different entities affiliated to the cloud platform. For example, the functions to be realized by the receiving unit 42 and the storage unit 44 are realized at a CPU, and the functions to be realized by the processing unit are realized at the client.

After the conditions of a patient with COPD are stabilized according to the diagnosis of a doctor, the patient may use the respirator to continuously monitor the physical conditions at home. In the embodiments of the disclosure, on the basis of the Internet, the household non-invasive respirators 12 and 14 or the therapy respirator 16 in the hospital that upload data in real time, and a cloud platform that supports real-time uploading of the user respiration data, an on-line data analysis system can be established to monitor the development conditions of the respiratory diseases of the patient in real time. For example, the cloud platform consists of the respirators 12, 14 and 16, the cloud sever 20 and an optional database 22 as shown in FIG. 1.

Clinical experience shows that the development of the conditions of the patient with the COPD can be incompletely reflected through the user data generated by the respirators, and the main symptoms of the patients suffering from the AECOPD need to be diagnosed by the doctor face to face, which means that whether or not the patients suffer the AECOPD depends on the diagnosis of the doctor instead of direct or individual data of the medical devices such as the respirators. In addition, the judgment standards that the on-line analysis system employs to analyze and judge various states during the development of the conditions of the patient also need to be adjusted along with the development of the conditions of the patients by the doctor according to the previous massive monitoring data including the user respiration data, for example the adjustment on the respirator index range of the stable state of the patient with COPD. Therefore, the above mentioned on-line medical analysis system provides references only, and the final diagnosis of the patients' conditions needs cooperation with traditional off-line delay diagnosis system to achieve a timely and accurate diagnosis and therapy effect.

Therefore, in order to obtain an accurate diagnosis result in whether or not the patient with COPD enters the AECOPD state, it is insufficient to depend on the on-line data analysis which is carried out at the cloud server 20 in the embodiments of the disclosure, and an off-line diagnosis system is needed to realize timely and accurate diagnosis on the patient.

According to an embodiment of the disclosure, the doctor needs to set or re-set the judgment on various use data of the on-line analysis system before the patient uses the non-invasive respirator 12 or 14 at home or before the patient whose conditions are stabilized leaves the hospital, goes back home and keeps on using the non-invasive respirator, thus starting a new on-line system monitoring cycle of the patient. After one monitoring cycle begins, the patient should use the non-invasive respirator every day, and connects the respirator to the Internet to upload the user respiration data to the cloud platform.

When the conditions are in a stable state period, the patient needs regular return visits, and after re-diagnosing the patient, the doctor needs to adjust the judgment standard on the user respiration data for the on-line system according to all monitored data of the patient from the previous return visit to the current return visits.

In accordance with various embodiments of the disclosure, once determining that the user respiration data of the patient are abnormal, the on-line analysis system sends an alarm, and the doctor and/or the patient can receive the alarm signal from the cloud platform. The patient should visit the doctor in time after receiving the alarms, and the doctor makes a further diagnosis on the patient's conditions to determine whether or not the patient needs to be treated in hospital or the judgment standards of the on-line system needs to be merely adjusted.

In accordance with a specific embodiment of the disclosure, the doctor can determine the judgment standards of the on-line system for various conditions of the patient at the beginning of the on-line monitoring and analysis cycle. The on-line judgment standards include the judgment standards on the stable state of the patient, the judgment standards on the slightly abnormal state of the patient, and the judgment standards on the severely abnormal state of the patient. The cloud platform performs statistical operations on the use data of the patient every 24 hours, and uses the results as the patient's data statistical value of the current day. Optionally, the validity of the data in the 24 hours will be judged before the statistical operations. For example, if the use time of the current day is less than 4 hours, and the air leaking amount does not exceed 30 LPM, the data of the current day are determined to be valid data; and if the data are invalid, the statistical operation is not carried out and it is regarded that no use data is generated in the 24 fours. It should be understood that, the starting point and ending point of the 24 hours are adjustable, for example, the 24-hour cycle lasts from 19:00 of the current day to 19:00 of the next day, or lasts from 9:00 of the current day to 9:00 of the next day.

In this embodiment, the conditions of the patient are determined to be stable or abnormal on the basis of the statistical data of the cloud platform for every 24 hours, wherein the statistical data are obtained on the basis of the user respiration data uploaded by the respirator that is used by the user, for example, statistical data include respiration frequency (RR), tidal volume (Vt), the ratio (RR/Vt) of the respiration frequency to the tidal volume, percentage of user triggering the respirator, percentage of user switching the respirator, respirator used time in one uploading cycle, blood oxygen saturation degree (SpO2), etc. It should be understood that according to the data recorded by the non-invasive respirators, the patient's conditions can also be judged on the basis of the data of more user respiration state indices or other user physical state indices.

For the judgment on the normal state and abnormal state of various statistical data, the setting of the determining standards may be described by taking the above mentioned statistic data as examples.

For the respiration frequency RR, if |RR−RR stable state value|>RR stable state value×30%, RR is judged to be severely abnormal; if RR stable state value×20%<|RR−RR stable state value|>RR stable state value×30%, RR is judged to be slightly abnormal.

For the tidal volume Vt, if (Vt−Vt stable state value)<−1×(Vt stable state value×30%), or (Vt−Vt stable state value)>(Vt stable state value×100%), Vt is judged to be severely abnormal; if −1×(Vt stable state value×30%)<(Vt−Vt stable state value)<−1×(Vt stable state value×20%), or (Vt stable state value×70%)<(Vt−Vt stable state value)<(Vt stable state value×100%), Vt is judged to be slightly abnormal.

For the percentage of user triggering the respirator, if (percentage of user triggering the respirator−stable state value of percentage of user triggering the respirator)<−1×(stable state value of percentage of user triggering the respirator×30%), the percentage of user triggering the respirator is judged to be severely abnormal; if −1×(stable state value of percentage of user triggering the respirator×30%)<(percentage of user triggering the respirator−stable state value of percentage of user triggering the respirator)<−1×(stable state value of percentage of user triggering the respirator×20%), the percentage of user triggering the respirator is judged to be slightly abnormal.

For the percentage of user switching the respirator, if (percentage of user switching the respirator−stable state value of the percentage of user switching the respirator)<−1×(stable state value of the percentage of user switching the respirator×30%), the percentage of user switching the respirator is judged to be severely abnormal; if −1×(stable state value of the percentage of user switching the respirator×30%)<(percentage of user switching the respirator−stable state value of the percentage of user switching the respirator)<−1×(stable state value of the percentage of switching of the respirator by the user×20%, the percentage of user switching the respirator is judged to be slightly abnormal.

For the respirator used time in one uploading cycle, if |respirator used time in every uploading cycle−stable state value of respirator used time in one uploading cycle|>stable state value of respirator used time in one uploading cycle× 50% for three consecutive uploading cycles, the respirator used time in one uploading cycle is judged to be severely abnormal; if stable state value of the respirator used time in one uploading cycle×30%<|respirator used time in every uploading cycle−stable state value of respirator used time in one uploading cycle|>stable state value of respirator used time in one uploading cycle×50%, the respirator used time in one uploading cycle is judged to be slightly abnormal.

For the blood oxygen saturation degree SpO2, if (SpO2−stable state value of SpO2)<−1 (stable state value of SpO2× 5%), SpO2 is judged to severely abnormal; and if −1×(stable state value of SpO2×5%)<(SpO2−stable state value of SpO2)<−1 (stable state value of SpO2×3%), SpO2 is judged to be slightly abnormal.

In another embodiment, for the daily statistical data, among the three static values, namely RR, Vt and SpO2, if RR and Vt are judged to be severely abnormal at the same time, or SpO2 is judged to be severely abnormal, or the three statistical values are judged to be severely abnormal at the same time, then the data of the current day are judged to be severely abnormal; if RR and Vt are judged to be slightly abnormal, or SpO2 is judged to be slightly abnormal, or the three statistical values are judged to be slightly abnormal at the same time, then the data of the current day are judged to be slightly abnormal.

In this embodiment, if the statistical data of a certain day are judged to be severely abnormal, then the cloud platform needs to send an alarm on the data of the current day and to inform the doctor and/or the patient. If the statistical data of a certain day are judged to be slightly abnormal, then the cloud platform needs to check the statistical data of the recent five days; if the statistical data of at least three of the five days are judged to be slightly abnormal, or the statistical data of the recent three days are continuously judged to be slightly abnormal, the cloud platform needs to send an alarm on the number of days and to inform the doctor and/the patient.

According to one embodiment of the disclosure, the operations of the cloud platform can be executed by the cloud server, wherein the operations include judging the abnormalities of the user respiration data and sending an alarm. According to another embodiment of the disclosure, the operations of the cloud platform can be executed by a special client, wherein the operations include judging the abnormalities of the user respiration data and sending an alarm.

For the off-line diagnosis system, after the cloud platform sends an alarm, the patient should contact the doctor in time and then the doctor diagnoses the conditions of the patient face to face; or the doctor actively diagnoses the patient face to face. If the patient may suffer AECOPD soon and needs therapy in the hospital according to the judgment of the doctor, then the current monitoring cycle of the on-line system is ended by the doctor; after the patient leaves the hospital, the doctor adjusts the stable state judgment standards of all statistical respiration data values of the on-line system, and then the next monitoring cycle of the on-line system may begin. If the patient is merely in a fluctuating period of the stable COPD state according to the judgment of the doctor, the current monitoring cycle of the on-line system continues, but the doctor needs to adjust the stable state judgment standards of all the statistical values of the on-line system. Additionally, the data in the stable state value set of a user may fluctuate; an initial state value set of the next cycle of the user may be set according to the weighted averages of all parameters in the deemed stable state period of the previous cycle of the user, and optionally, the doctor makes fine tuning on this basis.

The analysis of the user respiration data set on the cloud platform can be completed at the cloud server 20 as shown in FIG. 2, wherein the user respiration data set is uploaded every 24 hours by the respirator that is used by the user. The receiving unit 42 of the cloud server 20 is configured to receive the user respiration data from the respirator 12, 14 or 16, and may store the data into the storage unit 44 of the cloud server 20 or into the database 22 in connection with the storage unit 44. The processing unit 46 of the cloud server 20 is configured to acquire the user respiration data set sent by the user of the respirator device within 24 hours from the storage unit 44 or from the database 22, statistically analyze the user respiration data set on the basis of the stable state value set of the user, and after confirming the statistical analysis result that user respiration data set meets the data abnormal standard, send an alarm signal, send an alarm signal. As an example, the alarm signal can be sent to the terminal device of the user or the computer of the doctor, and the forms of the alarm signal include, but are not limited to, text message sent to the terminal device of the patient, alarm indications sent to the computer display of the doctor, or email sent to the doctor, etc.

It should be understood that, the user respiration data set received every 24 hours is statistically analyzed in the above embodiment, but in other embodiments, 10 hours every night (corresponding to the default sleep period of the patient), for example the period from 20:00 in night from 6:00 in morning, or every 48 hours, may be used as one uploading cycle or analysis cycle of the user respiration data.

In the above embodiment, under the condition that the statistical data of a certain day are judged to be slightly abnormal, the cloud platform needs to check if the statistical data of at least three of the five days are judged to be slightly abnormal, or the statistical data of the recent three days are continuously judged to be slightly abnormal. It should be understood that, the above mentioned five days and three days are merely examples, and this parameter can be re-set by the doctor according to the specific conditions of the patient.

According to the embodiment of the disclosure, the respirator 12, 14 or 16 may upload the user respiration data in real time or regularly, for example, the respirator uploads the data once in one uploading cycle.

According to the embodiment of the disclosure, the processing unit 46 in the cloud server 20 may also be configured to analyze the validity of the user respiration data set sent by the respirator device in one uploading cycle, and does not statistically analyze the user respiration data set which does not conform to the validity standard. Optionally, such pretreatment step may also be executed at the respirator 12, 14 or 16.

According to the embodiment of the disclosure, the above mentioned severe data abnormal standard, slight data abnormal standard or validity analysis standard may be based on the experience knowledge of the doctor, and the doctor obtains the experience knowledge through a great number of experiments according to different conditions of the patient.

According to the embodiment of the disclosure, the user respiration data set uploaded by the respirator may include one or more of respiration index data selected from the respiration frequency (RR), tidal volume (Vt), the ratio (RR/VT) of the respiration frequency to the tidal volume, percentage of user triggering the respirator, percentage of user switching the respirator, respirator used time in one uploading cycle and blood oxygen saturation degree (SpO2). Similarly, the stable state value set of the user in a certain period of time is also obtained on the basis of the above mentioned respiration indices. The above embodiments describe the data analysis and alarming process of the possible AECOPD of the patient with the COPD on the basis of the respiration data of the above mentioned types, but the on-line user respiration data analysis method for the cloud platform in the embodiment of the disclosure may also apply to data analysis of other respiratory diseases (for example, asthma, trachitis, pulmonary heart disease, etc.), and combined with the off-line diagnosis systems for other diseases, to diagnose the diseases of the types.

According to the embodiment of the disclosure, the cloud server 20 may send an alarm signal to the user of the respirators 12 and 14, or send an alarm signal to the doctor, or send an alarm signal to the watch man at the cloud server 20. The forms of the alarm signal may include audio, video and text notifications, for example, text message or multimedia message sent to the registered phone or instant messaging tools of the user.

It should be understood that, the above mentioned functions executed at the cloud server 20 in the disclosure can be realized with software, hardware or combination of software and hardware. The hardware may be realized with special logic; the software may be stored in a memory, and executed by an appropriate instruction execution system, for example, a microprocessor, a personal computer (PC) or a large computer. In some embodiments, the disclosure is realized as software which includes, but is not limited to firmware, resident software, micro-codes, etc.

Figure 3:
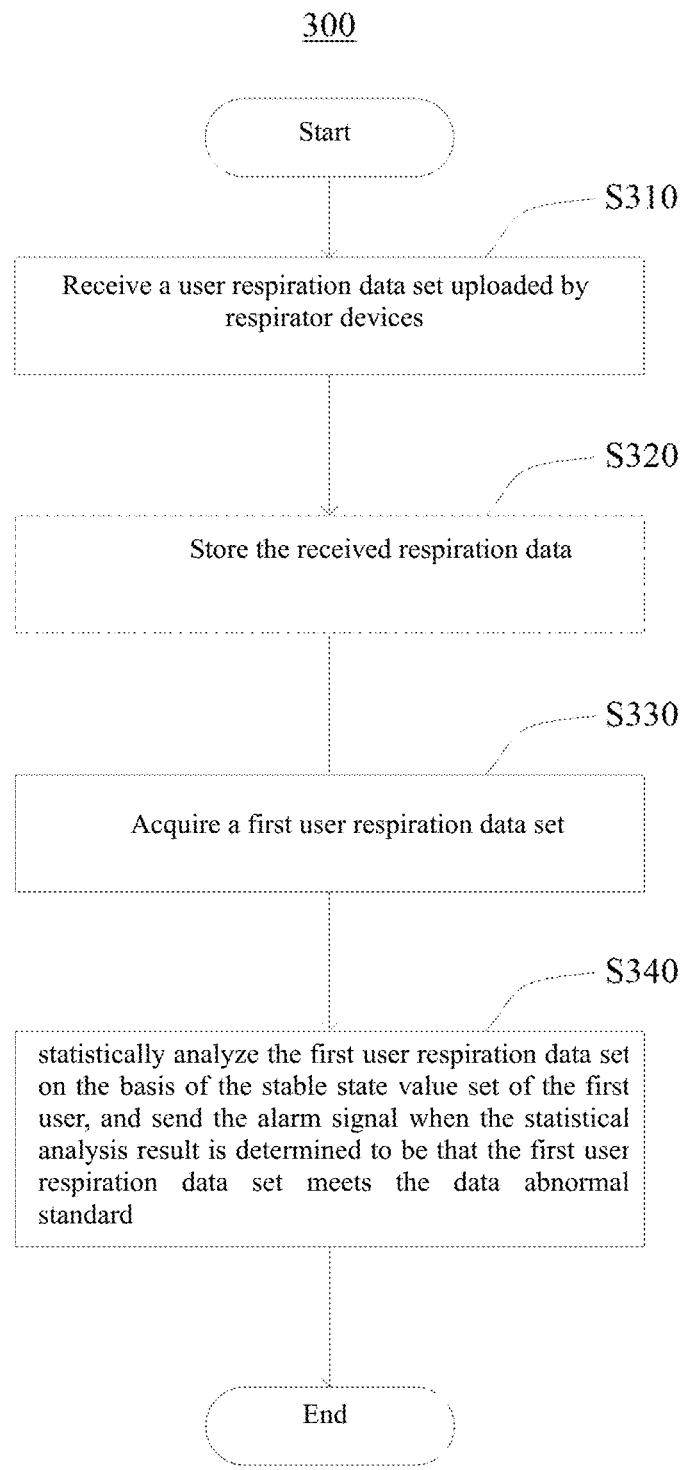
FIG. 3 is a flow chart of a method for alarming abnormal user respiration data set in one embodiment according to the disclosure.

FIG. 3 is a flow chart of a method 300 for alarming abnormal user respiration data set in the embodiment of the disclosure.

Step 310, receive at least one user respiration data set sent by at least one respirator device in at least one uploading cycle.

Step 320, store the received at least one user respiration data set in a memory or an external database.

Step 330, acquire a first user respiration data set which is sent by a user of one respirator device among at least one respirator device in one uploading cycle.

Step 340, statistically analyze the first user respiration data set on the basis of the stable state value set of the first user, and when the statistical analysis result is determined to be that the first user respiration data set meets the data abnormal standard, send an alarm signal.

Figure 4:
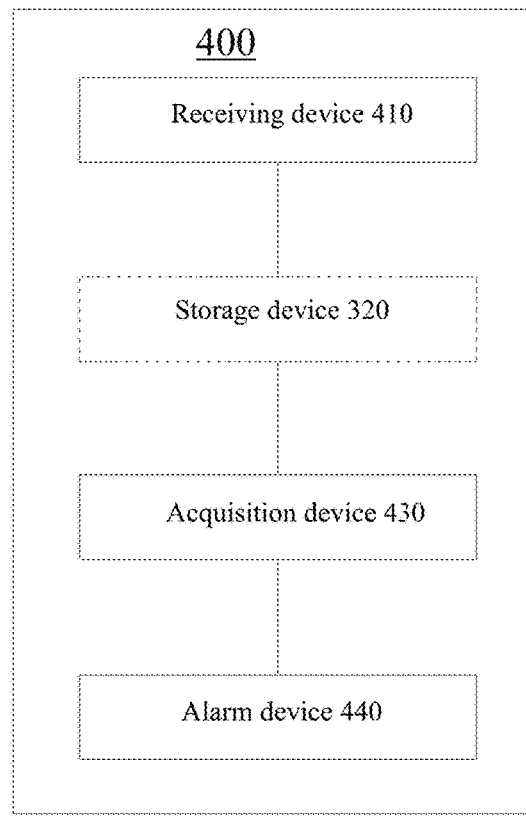
FIG. 4 is a flow chart of a device for alarming abnormal user respiration data set in one embodiment according to the disclosure.

FIG. 4 is a flow chart of a device 400 for alarming abnormal user respiration data set in the embodiment of the disclosure. The device 400 includes: a receiving device 410 for receiving at least one user respiration data set which is sent by at least one respirator device in at least one uploading cycle; a storage unit 420 for storing the received at least one user respiration data set in a memory or an external database; an acquisition device 430 for acquiring a first user respiration data set which is sent by a user of one respirator device among at least one respirator device in one uploading cycle; an alarm device 440 for statistically analyzing the first user respiration data set on the basis of a stable state value set of the user, and after confirming the statistical analysis result that the first user respiration data set meets a data abnormal standard, sending an alarm signal.

It should be understood that, terms "first", "second", "Nth", etc. may be used to describe various elements, but the elements should not be limited by the terms because the terms are merely used for distinguishing one element from another.

The disclosure may also be configured as computer program products of a computer readable storage media, including computer program codes. When the computer program codes are executed by the processor, the processor can realize warning of the abnormal user respiration data set as described in the embodiment of the text according to the method of the embodiment of the disclosure. The computer storage medium may be any physical media, for example, floppy disk, CD-ROM, DVD, hard disc drive, and even network media, etc.

Figure 5:
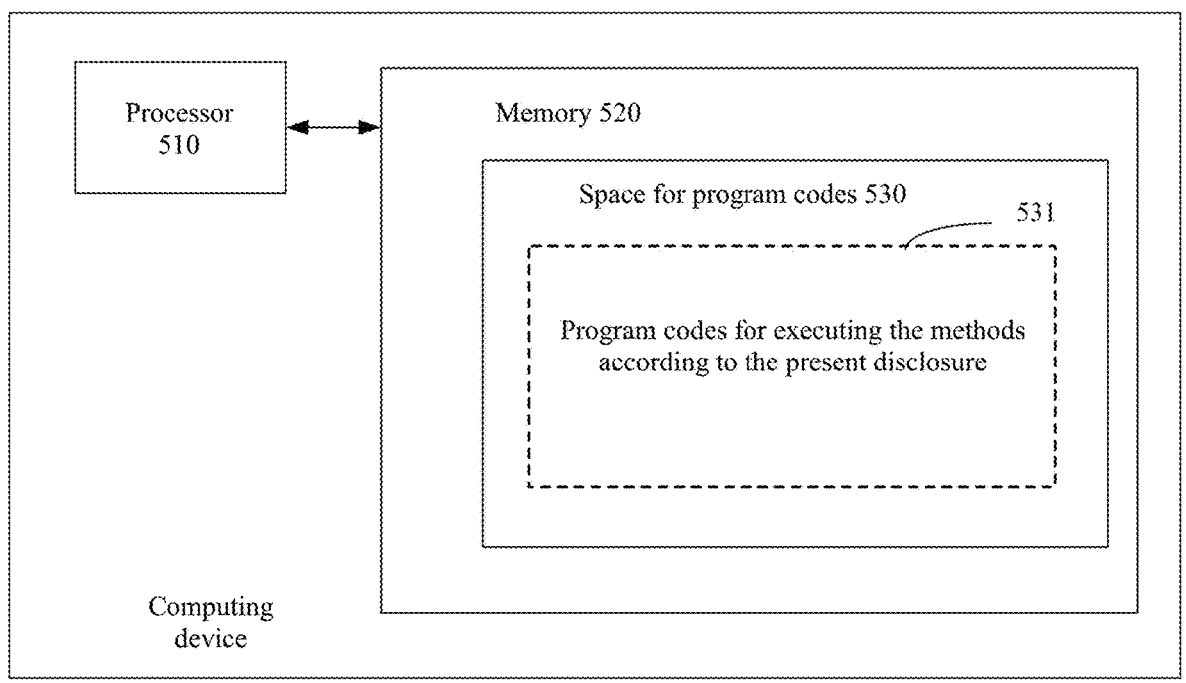
FIG. 5 is a block diagram of a computing device for executing the method for alarming abnormal user respiration data set according to the present disclosure.
Figure 6:
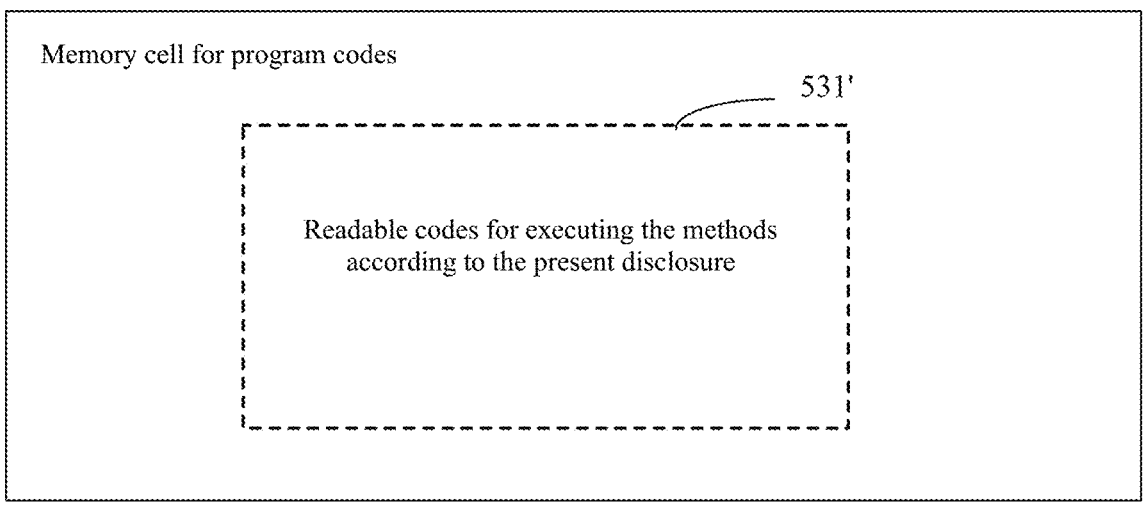
FIG. 6 illustrates a memory cell for holding or carrying program codes for realizing the method for alarming abnormal user respiration data set according to the disclosure.

For example, FIG. 5 illustrates a block diagram of a computing device for executing the method for warning the abnormal user respiration data according to the disclosure. For example, the computing device may include cloud platform devices, a server, respirator devices, etc. Traditionally, the computing device includes a processor 510 and a computer program product or a computer readable medium in form of a memory 520. For example, the processor may include processing units of the cloud platform. The memory 520 could be electronic memories such as flash memory, EEPROM (Electrically Erasable Programmable Read-Only Memory), EPROM or ROM, for example the storage device of the cloud platform. The memory 520 has a memory space 530 for executing program codes 531 of any steps in the above methods. For example, the storage space 530 for program codes can include the program codes 531 for respectively executing all steps of the above methods. The programs can be read from one or more program products or written into one or more program products. The program products include program code carriers such as memory cards. Such program products are usually portable or fixed storage units as shown in FIG. 6. The memory cells can have storage segments, storage space, etc. similar to the memories 520 in the computer device as shown in FIG. 5. The program codes can be compressed in a proper form. Usually, the memory cell includes computer readable codes 531' which can be read for example by processors 510. When these codes are operated on the computing device, the computing device may execute respective steps in the method as described above.

It should also be understood that, the flow chart in FIG. 3 and block diagram of FIG. 4 illustrate the functions and operations of possible realization of the method or computer program product in all embodiments of the disclosure, wherein the functions and operations marked with dotted lines are optional functions and operations. Every square block in the flow chart and block diagram may represent a module, a program segment, or a code section, wherein the module, the program section, or the code section includes one or more executable instructions for realizing preset logic functions. It should also be noted that, in some alternative realizations, the functions marked in the square blocks may be executed in a sequence different from that marked in the drawings. For example, two consecutive square blocks actually may be basically executed in parallel, or executed in a reverse sequence, which depends on the functions involved. For example, steps S310 and S320 may be different from the step S330 and step S340 in the execution sequence. When the respirator uploads the user respiration data in real time, the data receiving and storing functions of steps S310 and S320 are executed in real time; when one data uploading cycle ends, steps S330 and S340 are executed to analyze the data that are received in the uploading cycle.

It should also be noted that, the contents in every square block of the block diagram and/or flow chart and the contents of the combinations of the square blocks of the block diagram and/or flow chart can be realized with special hardware-based system for executing specified functions or operations, or realized with combinations of special hardware and computer instructions.

According to various embodiments of the disclosure, the statistically data needed to be analyzed are all uploaded by the household non-invasive respirator used by the patient to the cloud platform, and are automatically analyzed by the cloud platform. The cloud platform displays the analysis result or report. The whole process does not include steps that need to be completed by the patient, so the operation is very easy for the patient and the error rate is relatively low.

At the same time, the on-line analysis solutions of various embodiments of the disclosure need to be combined and cooperate with a set of off-line judgment system to accurately diagnose whether a patient suffers AECOPD. According to the implementation of the disclosure, attention is paid to the real-time respiration data of the patient, comprehensive analysis of massive data is carried, and only when the respiration data are judged to be abnormal, the warning for seeking medical help is sent to the patient. The disclosure utilizes the advantage that the cloud platform may process data in real time and employs the traditional off-line diagnosis method that needs a relatively huge amount of data, so the timeliness and accuracy of the patient diagnosis and therapy are greatly improved, the pains of and burdens on the patients are relieved, and the consumption and cost of the doctor and hospital are reduced at the same time.

The description of the disclosure is given for the purposes of disclosure and depiction, but does not aim to exhaust or limit the invention in the disclosed form. Those skilled in the art can conceive of many modifications and changes after reading the contents of the present disclosure. All embodiments described above can be used individually or in combination, unless otherwise clearly specified in the context.

Therefore, the embodiments are selected and described for better explaining the principle and practical applications of the disclosure and for better understanding of the contents by other people in the art. Namely, all modifications and replacements made without departing from the spirit of the disclosure will fall within the protective scope of the claims of the present disclosure.

What is claimed is:

1. A system for evaluating acute exacerbation of chronic obstructive pulmonary disease, comprising:
   a receiving unit configured to receive at least one user respiration data set sent by at least one respirator device in at least one uploading cycle;
   a storage unit configured to store the at least one user respiration data set sent by the at least one respirator device in at least one uploading cycle, wherein the receiving unit is further configured to store the at least one user respiration data set in the storage unit; and
   a processing unit configured to:
      communicate with the storage unit to acquire a first user respiration data set of the at least one user respiration data set sent by a user of one respirator device among the at least one respirator device in one uploading cycle from the storage unit, the first user respiration data set comprising parameters of a respiration frequency, a tidal volume, a ratio of the respiration frequency to tidal volume, a percentage of user triggering the respirator device, a respirator device usage time, and a blood oxygen saturation degree in one uploading cycle;

perform a validity analysis on the first user respiration data set to yield validity analysis information and update the first user respiration data set with the validity analysis information based on a determination that the first user respiration data set meets a validity standard, wherein the validity standard comprises the first user respiration data set including at least four hours of user respiration data of the user using the at least one respirator device, and an air leaking amount does not exceed 30 L/min when the user uses the at least one respirator device;

statistically analyze each parameter of the first user respiration data set on the basis of a stable state value set of a previous monitoring period of the user to determine if the first user respiration data set meets a severe data abnormal standard or a slight abnormal standard;

when the first user respiration data set meets the severe abnormal standard, send a first audio, video or text notification; and when the first user respiration data set meets the slight abnormal standard, the processing unit is further configured to acquire a previous N−1 respiration data set sent by the user in N−1 uploading cycle previous to the uploading cycle; determine if M user respiration data sets in the first user respiration data set and in the previous N−1 user respiration data set meet the slight abnormal standard, wherein N is an integer larger than 2, and M is an integer less than N; and send a second audio, video or text notification when M user respiration data sets in the first user respiration data set and in the previous N−1 user respiration data set meet the slight abnormal standard, wherein the severe abnormal standard comprises at least one condition selected from the group consisting of:
  a) a deviation of the respiration frequency from a respiration frequency stable state value is larger than 30% of the respiration frequency stable state value;
  b) the tidal volume deviates from a tidal volume stable state value, and a reduction of the tidal volume with respect to the tidal volume stable state value is larger than 30% of the tidal volume stable state value, or an increment of the tidal volume with respect to the tidal volume stable state value is larger than 100% of the tidal volume stable state value;
  c) the percentage of user triggering the respirator device deviates from a stable state value of the percentage of user triggering the respirator device, and a reduction of the percentage of user triggering the respirator device with respect to the stable state value of the percentage of user triggering the respirator device is larger than 30% of the stable state value of the percentage of user triggering the respirator device;
  d) the deviations of the respirator device used time in three consecutive uploading periods from a stable state value of the respirator device used time in one uploading cycle are larger than 50% of the stable state value of the respirator device used time in one uploading cycle; and
  e) the blood saturation degree deviates from a stable state value of the blood saturation degree, and a reduction of the blood saturation degree with respect to the stable state value of the blood saturation degree is larger than 5% of the stable state value of the blood saturation degree; and wherein the slight abnormal standard comprises at least one condition selected from the group consisting of:
  f) the deviation of the respiration frequency from a respiration frequency stable state value is larger than 20% and less than 30% of the respiration frequency stable state value;
  g) the tidal volume deviates from a tidal volume stable state value, and a reduction of the tidal volume with respect to the tidal volume stable state value is larger than 20% and less than 30% of the tidal volume stable state value, or an increment of the tidal volume with respect to the tidal volume stable state value is larger than 70% and less than 100% of the tidal volume stable state value;
  h) the percentage of user triggering the respirator device deviates from a stable state value of the percentage of user triggering the respirator device, and a reduction of the percentage of user triggering the respirator device with respect to the stable state value of the percentage of user triggering the respirator device is larger than 20% and less than 30% of the stable state value of the percentage of user triggering the respirator device;
  i) the deviations of the respirator device used time in three consecutive uploading periods from a stable state value of the respirator device used time in one uploading cycle are larger than 30% and less than 50% of the stable state value of the respirator device used time in one uploading cycle; and
  j) the blood saturation degree deviates from a stable state value of the blood saturation degree, and a reduction of the blood saturation degree with respect to the stable state value of the blood saturation degree is larger than 3% and less than 5% of the stable state value of the blood saturation degree.

2. The system according to claim 1, wherein the uploading cycle is 24 hours.

3. The system according to claim 1, wherein the respiration data in the stable state value set of the same user is fluctuating.

4. A method for alarming abnormal user respiration data to evaluate acute exacerbation of chronic obstructive pulmonary disease, comprising:

receiving at least one user respiration data set sent by at least one respirator device in at least one uploading cycle;

storing the at least on data set sent by the at least one respirator device in a storage unit;

acquiring a first user respiration data set of the at least one user respiration data set sent by a user of one respirator device among at least one respirator device in one uploading cycle from the storage unit, the first user respiration data set comprising parameters of a respiratory frequency, a tidal volume, a ratio of the respiration frequency to the tidal volume, a percentage of user triggering the respirator device, a respirator device usage time, and a blood oxygen saturation degree in one uploading cycle;

performing a validity analysis on the first user respiration data set to yield validity analysis information and update the first user respiration data set with the validity analysis information based on a determination that the first user respiration data set meets a validity standard, wherein the validity standard comprises the first user respiration data set including at least four hours of user respiration data of the user using the at least one respirator device, and an air leaking amount does not exceed 30 L/min when the user uses the at least one respirator device;

statistically analyzing each parameter of the first user respiration data set on the basis of a stable state value set of a previous monitoring period of the user to determine if the first user respiration data set meets a severe data abnormal standard or slight abnormal standard; and when the first user respiration data set meets the severe abnormal standard, sending a first audio, video or text notification, wherein the severe abnormal standard comprises at least one condition selected from the group consisting of:

a) a deviation of the respiration frequency from a respiration frequency stable state value is larger than 30% of the respiration frequency stable state value;

b) the tidal volume deviates from a tidal volume stable state value, and a reduction of the tidal volume with respect to the tidal volume stable state value is larger than 30% of the tidal volume stable state value, or an increment of the tidal volume with respect to the tidal volume stable state value is larger than 100% of the tidal volume stable state value;

c) the percentage of user triggering the respirator device deviates from a stable state value of the percentage of user triggering the respirator device, and a reduction of the percentage of user triggering the respirator device with respect to the stable state value of the percentage of user triggering the respirator device is larger than 30% of the stable state value of the percentage of user triggering the respirator device;

d) the deviations of the respirator device used time in three consecutive uploading periods from a stable state value of the respirator device used time in one uploading cycle are larger than 50% of the stable state value of the respirator device used time in one uploading cycle; and e) the blood saturation degree deviates from a stable state value of the blood saturation degree, and a reduction of the blood saturation degree with respect to the stable state value of the blood saturation degree is larger than 5% of the stable state value of the blood saturation degree; or when the first user respiration data set meets a slight abnormal standard, acquiring a previous N−1 respiration data set sent by the user in N−1 uploading cycle previous to the uploading cycle; determining if M user respiration data sets in the first user respiration data set and in the previous N−1 user respiration data set meet the slight abnormal standard, wherein N is an integer larger than 2, and M is an integer less than N; and sending a second audio, video or text notification when M user respiration data sets meet the slight abnormal standard, wherein the slight abnormal standard comprises at least one condition selected from the group consisting of:

f) the deviation of the respiration frequency from a respiration frequency stable state value is larger than 20% and less than 30% of the respiration frequency stable state value;

g) the tidal volume deviates from a tidal volume stable state value, and a reduction of the tidal volume with respect to the tidal volume stable state value is larger than 20% and less than 30% of the tidal volume stable state value, or an increment of the tidal volume with respect to the tidal volume stable state value is larger than 70% and less than 100% of the tidal volume stable state value;

h) the percentage of user triggering the respirator device deviates from a stable state value of the percentage of user triggering the respirator device, and a reduction of the percentage of user triggering the respirator device with respect to the stable state value of the percentage of user triggering the respirator device is larger than 20% and less than 30% of the stable state value of the percentage of user triggering the respirator device;

i) the deviations of the respirator device used time in three consecutive uploading periods from a stable state value of the respirator device used time in one uploading cycle are larger than 30% and less than 50% of the stable state value of the respirator device used time in one uploading cycle; and j) the blood saturation degree deviates from a stable state value of the blood saturation degree, and a reduction of the blood saturation degree with respect to the stable state value of the blood saturation degree is larger than 3% and less than 5% of the stable state value of the blood saturation degree.

* * * * *